United States Patent [19]
Skog

[11] Patent Number: 5,740,796
[45] Date of Patent: Apr. 21, 1998

[54] VENTILATOR SYSTEM AND METHOD FOR OPERATING SAME

[75] Inventor: Göran Skog, Bromma, Sweden

[73] Assignee: Siemens Elema AB, Solna, Sweden

[21] Appl. No.: 743,737

[22] Filed: Nov. 6, 1996

[30] Foreign Application Priority Data

Dec. 1, 1995 [SE] Sweden .................................. 9504313

[51] Int. Cl.$^6$ .................................................. A61M 16/00
[52] U.S. Cl. .......................... 128/204.23; 128/204.18; 128/207.14
[58] Field of Search ..................... 128/200.23, 204.18, 128/204.21, 204.23, 204.26, 205.23, 205.24, 207.14, 207.15

[56] References Cited

U.S. PATENT DOCUMENTS

| | | | |
|---|---|---|---|
| 4,265,237 | 5/1981 | Schwanbom et al. | 128/204.24 |
| 4,318,399 | 3/1982 | Berndtsson | 128/204.23 |
| 4,565,194 | 1/1986 | Weerda et al. | 128/204.23 |
| 5,400,778 | 3/1995 | Jonson et al. | 128/205.19 |
| 5,546,935 | 8/1996 | Champeau | 128/205.23 |

FOREIGN PATENT DOCUMENTS

| | | |
|---|---|---|
| WO 82/03014 | 9/1982 | WIPO . |
| WO 91/19526 | 12/1991 | WIPO . |
| WO 94/001571 | 1/1994 | WIPO . |

*Primary Examiner*—Vincent Millin
*Assistant Examiner*—Eric P. Raciti
*Attorney, Agent, or Firm*—Hill, Steadman & Simpson

[57] ABSTRACT

A ventilator system has an inspiratory line, an inspiratory pressure meter arranged to sense pressure in the inspiratory line, and expiratory line, an expiratory pressure meter arranged to sense pressure in the expiratory line, and a connector device for connecting a patient to the ventilator system. The connector device includes a first gas line connected to the inspiratory line, and a second gas line connected to the expiratory line so that gas will only be able to flow in one direction through the lines. Pressure in the lungs can accordingly be directly measured by the expiratory pressure meter during inspiration and by the inspiratory pressure meter during expiration.

12 Claims, 2 Drawing Sheets

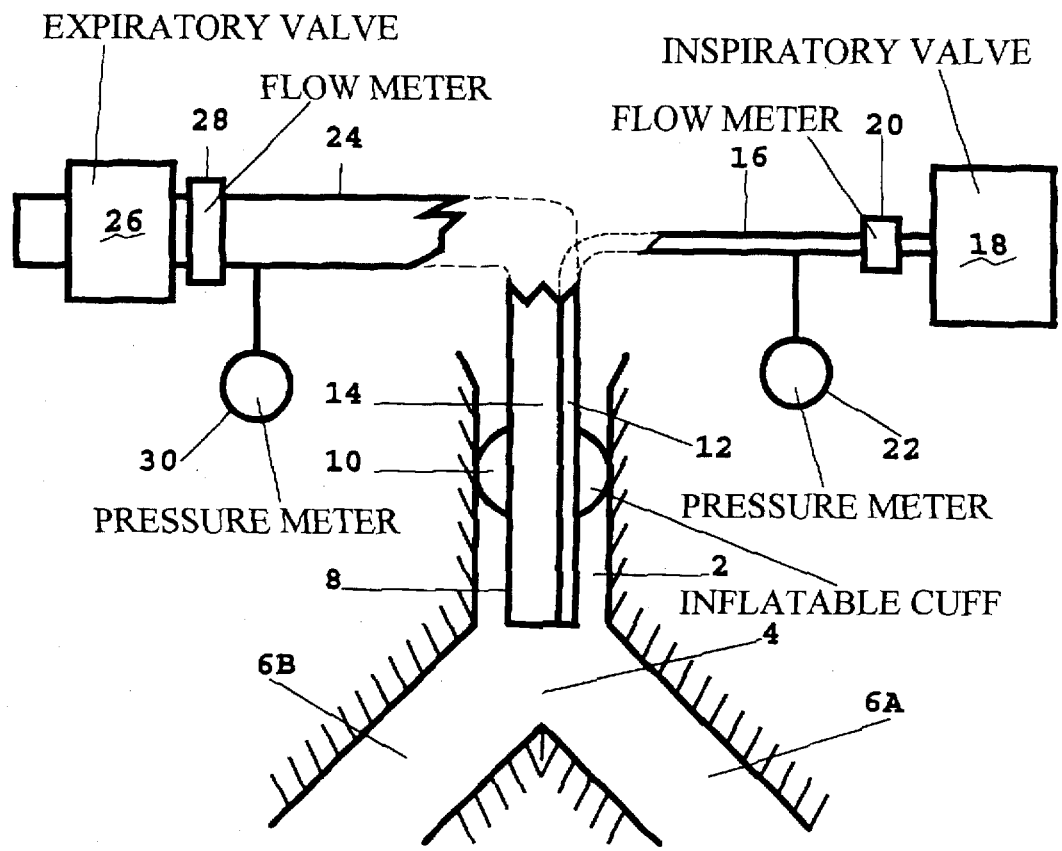
FIG. 1
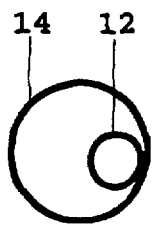  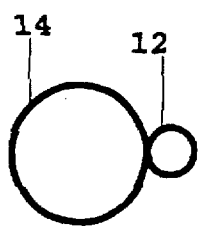  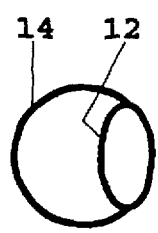
FIG. 2A　　　FIG. 2B　　　FIG. 2C

5,740,796

VENTILATOR SYSTEM AND METHOD FOR OPERATING SAME

BACKGROUND OF THE INVENTION

1. Field of the Invention

The present invention relates to a method, for use with a ventilator system, for measuring pressure in a lung system during respirator treatment in which gas is carried to the lung system during inspiration and carried away from the lung system during expiration.

The present invention also relates to a ventilator system of the type having an inspiratory line, and expiratory line, and expiratory pressure meter, arranged to sense pressure in the expiratory line, and a connector device, devised for placement at least in part in a patient's trachea, facing the carina, in order to connect the patient to the ventilator system.

2. Description of the Related Art

A ventilator system of the above general type is described in WO-91/19526 and includes a ventilator to which an inspiratory line and an expiratory line are connected. The inspiratory line and the expiratory line are attached, in ram, via a Y-piece to which a tracheal tube is also attached. The tracheal tube is intended for insertion into a patient's trachea in order to carry breathing gas to and from the patient's lungs. An inspiratory pressure meter is arranged in the ventilator unit to sense pressure in the ventilator systems inspiratory section and an expiratory pressure meter for sensing the pressure in the ventilator system's expiratory section.

Accurate sensing of pressure is important, the pressure in the patient's lung system in particular, i.e. pressure at the carina (the ridge separating the openings of the main bronchi at their junction with the trachea). Primarily as a result of the drop in pressure in the tracheal tube when breathing gas flows through it, the ventilator's pressure meters do not measure pressure in the lungs. Compensation for this drop in pressure must be made to obtain information on pressure at the carina, and determining this compensation can be difficult. The drop in pressure is dependent on, e.g., flow in the tracheal tube. A number of methods can be used for calculating compensation for the drop in pressure.

U.S. Pat. No. 4,265,237 describes a ventilator system in which a special pressure measurement tube is inserted into the tracheal tube to measure pressure in the lower part of the tracheal tube. If the pressure measurement tube is inserted all the way down to the carina, pressure can be measured there with good accuracy. Lockage of the pressure measurement tube by secretions and other materials formed in the patient's lungs and lower airways, however, is a problem which can occur in this type of measurement. This procedure therefore is very unreliable.

Swedish Published Application 430 213 descries a ventilator system with two ventilator units. One of the ventilator units is set up as an ordinary ventilator, i.e. With inspiratory and expiratory lines connected to a common tracheal tube. The second ventilator unit has a separate supply line arranged inside the tracheal tube. In principle, breathing gas can be supplied, via the supply line, from the second ventilator unit, and gas can be carried away from the patient via the tracheal tube and expiratory line. This ventilator system is provided with a pressure measurement tube, like the one described above, to measure pressure in the carina.

SUMMARY OF THE INVENTION

An object of the present invention is to provide a ventilator system which avoids the problems in known systems and wherein pressure measurements in the lungs can be performed simply and safely and with accurate results.

This object is achieved in accordance with the invention in a method wherein gas is delivered to the lung system via a separate firs gas line and removal of gas from the lung system is undertaken via a second separate gas line, and wherein pressure in the lung system is measured during inspiration by measurement of pressure in the second separate gas line.

This means that all gas flows to the patient's lungs through the first gas line during inspiration. Since no gas flows through the second line, no drop in pressure occurs across the second line. Pressure in the second gas line will then be the same as pressure at the carina. A pressure measurement at some point in the second gas line will then also designate pressure at the carina.

It is an embodiment of the method in accordance with the invention, pressure in the lung system is measured during expiration by measuring pressure in the first separate gas line.

In a corresponding manner as in inspiration, all gas expired during expiration flows through the second gas line. No gas then flows in the first gas line, so there is no drop in pressure in this line either. Measurement of pressure in the first gas line thus also yields the pressure at the carina. Since new gas flows through the first gas line in every inspiration, this line is kept free from secretions and the like.

A ventilator system is achieved in accordance with the invention in ventilator system having a connector device with a first gas line, connected to the inspiratory line, and a second gas line, connected to the expiratory line, these gas lines being arranged so gas only flows respectively through them in one direction, and pressure in the patient's lungs is measured during inspiration by means of an expiratory pressure meter.

BRIEF DESCRIPTION OF THE DRAWINGS

FIG. 1 shows a diagram of the relevant components in a ventilator system, connected to a patient, constructed according to the invention.

FIGS. 2A–2C respectively show different designs for a tracheal tube in the ventilator system according to the invention.

DESCRIPTION OF THE PREFERRED EMBODIMENTS

Figure 3:
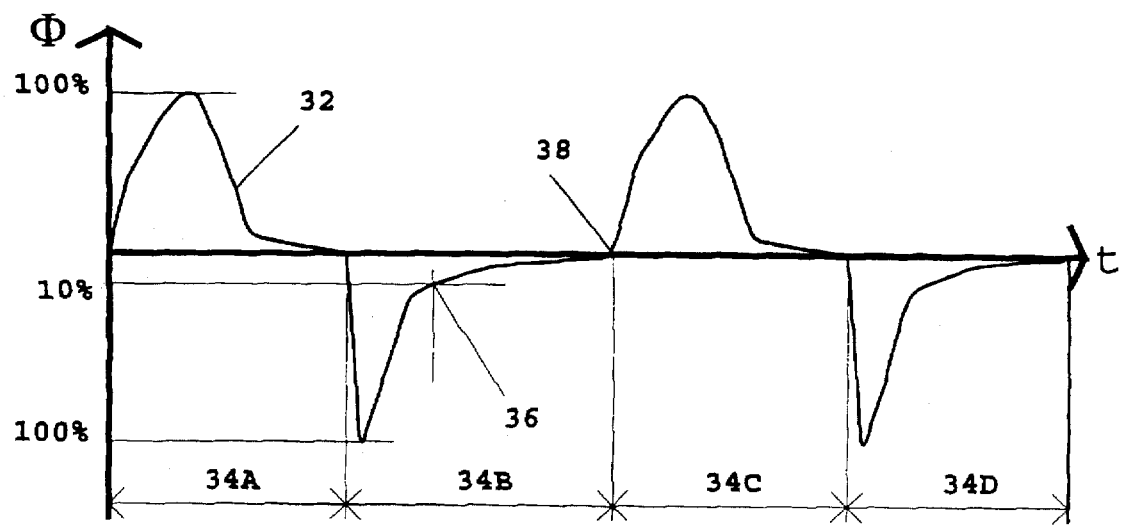
FIG. 3 shows breathing curves for a typical subject.

FIG. 1 shows the lower part of a patient's trachea 2. The trachea 2 opens onto the carina 4 from which the main bronchi 6A and 6B lead into the lungs. A tracheal tube 8 is in the trachea 2 and affixed with a cuff 10. The cuff 10 is inflatable and prevents gas from passing through the trachea around the tracheal tube 8. The tracheal tube 8 has a first gas line 12, through which breathing gas is supplied to the patient's lungs during inspiration, and a second gas line 14, through which breathing gas is carried away from the patient's lungs during expiration.

As shown in FIG. 1, the first gas line 12 is connected to an inspiratory line 16. The inspiratory line 16 is connected to an inspiratory valve 18 which regulates the supply of breathing gas to the inspiratory line 16. A flow meter 20 is arranged to measure the flow of breathing gas from the inspiratory valve 18, and an inspiratory pressure meter 22 is arranged to measure pressure in the inspiratory line 16.

In a corresponding manner, the second gas line 14 is connected to an expiratory line 24 which, in turn, is connected to an expiratory valve 26. The expiratory valve 26 regulates the flow of gas from the patient's lungs and/or pressure in the expiratory line 24 in the end phase of expiration. A second flow meter 28 is arranged in the expiratory line 24 to measure the flow of breathing gas, and an expiratory pressure meter 30 is arranged to measure pressure in the expiratory line 24.

The inspiratory valve 18, the first flow meter 20, the inspiratory pressure meter 22, the expiratory valve 26, the second flow meter 28 and the expiratory pressure meter 30 can all be arranged in a ventilator unit (not shown). One such ventilator could be, e.g., a Servo Ventilator 300, Siemens-Elema AB, Solna, Sweden. The ventilator unit may alternatively be a ventilator unit according to the previously cited document, WO 91/1956 (Servo Ventilator 900 C, Siemens-Elema AB).

The unique features of the invention are that gas to and from the patient respectively passes through completely separate gas lines 12 and 14 and, particularly, that pressure at the carina is measured with the expiratory pressure meter 30 during inspiration and vice-versa. In this manner, pressure at the carina 4 can be measured with much greater accuracy than in known systems. Moreover, no calculation program is needed to determine compensation for the drop in pressure etc. in the tracheal tube. During inspiration, when breathing gas is supplied via the inspiratory line 16 and the first gas line 12, no gas flows in the second gas line 14 and the expiratory line 24. The expiratory pressure meter 30 then measures pressure at the carina 4, since there is no drop in pressure in the expiratory line 24 and the second gas line 14.

A small flow is permissible in the second gas line 14, as long as the drop in pressure which then develops therein is negligible. Any drop in pressure can be measured with good accuracy when the flow is supplied in the first gas line 12, and pressure is measured in the second gas line 14.

In a corresponding manner, all gas flows through the second gas line 14 and the expiratory line 24 during expiration. No gas then flows through the first gas line 12 and the inspiratory line 16, so the drop in pressure across these lines is zero. The inspiratory pressure meter 22 then measures pressure at the carina 4.

The tracheal tube 8 with the first gas line 12 and the second gas line 14 can be devised in a number of ways, as shown in the tracheal tube cross-sections in FIGS. 2A, 2B and 2C. As in FIG. 1, FIG. 2A shows the first gas line 12 arranged inside the second gas line 14. The first gas line 2 can also be arranged parallel to and alongside the second gas line 14 (FIG. 2B) or integrated into the second gas line 14 (FIG. 2C). Additional embodiments of the tracheal tube 8, with two separate gas lines 12 and 14, can be simply achieved.

The embodiment with separate gas lines 12 and 14 also makes possible simpler pressure triggering in spontaneous breathing. Since the pressure meters 22 and 30 measure pressure at the carina 4, any attempt at spontaneous breathing by the patient will be detected in the form of a drop in pressure at the carina 4. An inspiration can then be immediately supplied to the patient. In a corresponding manner, any attempt at expiration by the patient is quickly detected as an increase in pressure in the carina 4, and an expiration can then be triggered in a simpler manner than in known systems.

The trachea normally forms a dead space, i.e. gas which is rebreathed at the start of an inspiration. The entire tracheal tube forms a dead space to an intubated patient. Another advantage of the separate administration and removal of breathing gas is that the system minimizes the dead space.

The pressure meters 22 and 30 can be simply checked against each other if pressure readings during inspiratory and expiratory pauses respectively and (when no gas flows through any of the lines 12, 14, 16 and 24) are compared.

Triggering inspirations on the basis of flow measurements instead of pressure measurements, or a combination thereof, is desired in certain instances. A continuous basic flow of gas is then usually supplied via the inspiratory line 16. Flow is affected when the patient attempts to inhale, and an inspiration is triggered when flow has been affected to a sufficient degree. To minimize the impact of basic flow on pressure measurements in the present ventilator system, the system is devised in a specific manner described in greater detail in connection with FIG. 3.

FIG. 3 is a flow and time diagram showing a breathing curve 32. In FIG. 3, the breathing curve 32 covers two breathing cycles, a first inspiration 34A, a first expiration 34B, a second inspiration 34C and a second expiration 34D. Peak values for inspiratory flows and expiratory flows were set at 100%. They can be measured from breathing cycle to breathing cycle. The second flow meter measures flow during expiration. When flow drops to a predefined percentage of the peak value for flow, a weak basic flow of breathing gas is activated from the inspiratory valve. In this instance, 10% of the peak value for flow during the current expiratory 34B was used as the defined percentage. The patient will then be able to trigger an inspiration based on flow measurement. When measured flow indicates a predefined inspiratory effort by the patient, as shown at point 38, the ventilator system is activated to supply an inspiration.

The basic flow supplied is small, and the drop in pressure in the second gas line 14 is therefore also small, so the pressure reading obtained by the expiratory pressure meter 30 can be used for relatively accurate determination of e.g. PEEP. A weighted value between the pressure measured by the inspiratory pressure meter 22 and the pressure measured by the expiratory pressure meter 30 can be used to attain greater accuracy.

The modest amount of breathing gas supplied during the latter part of expiration also conveys additional advantages. Gas evacuation of the lung is slight at the end of expiration and can be improved when the small additional gas flow supplied picks up some of the expired gas below the gas lines 12 and 14. In this manner, the volume of dead space can be further reduced and $CO_2$ flushed out of the lungs. This flow can be eliminated in the breaths in which measurements are made of the concentration of expired $CO_2$.

Limits other than 10% of the peak value for flow are also possible in determining when the basic flow is to be added.

Figure 4:
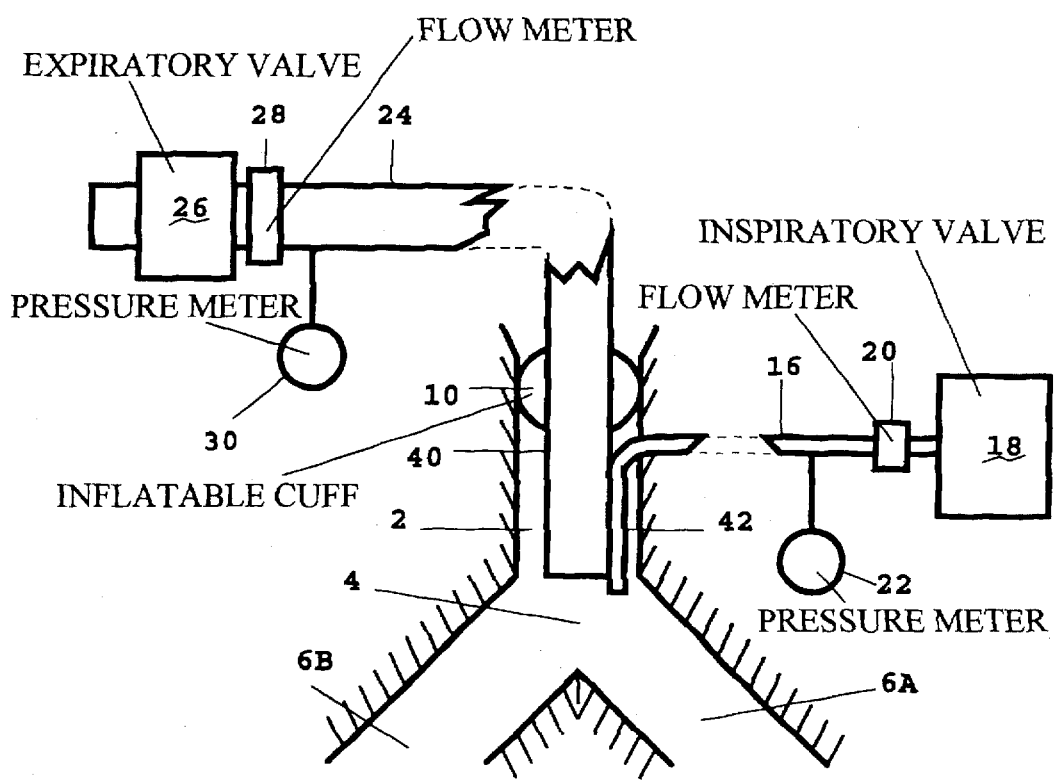
FIG. 4 shows an alternative design for the ventilator system according to the invention.

FIG. 4 shows an alternative embodiment of the ventilator system according to the invention. Components which can be identical have the same designations as in FIG. 1, and thus do not need to be described again. The major difference between the ventilator system according to FIG. 4 and the ventilator system according to FIG. 1 is that the ventilator in FIG. 4 has a separate tracheal tube 40, with only one gas channel, inserted into the patient's trachea 2 to carry away expired breathing gas in expiration. Gas supplied to the patient during inspiration is instead carried through a tracheotomy connector 42 to the patient's trachea 2. In this instance, the tracheal tube 40 can be made relatively short and even avoid, in principle, passing the patient's vocal cords and damaging them.

Although the invention has been described with respect to preferred embodiments, it is not to be so limited as changes and modifications can be made therein which are within the full intended scope of the invention as defined by the appended claims.

I claim as our invention:

1. A method for measuring pressure in a lung system of a subject during respirator treatment of said subject comprising the steps of:

conducting gas to said lung system during inspiration in a first gas line;

conducting gas away from said lung system during expiration in a second gas line, separate from said first gas line; and measuring pressure in said lung system by measuring pressure in said second gas line during inspiration.

2. A method as claimed in claim 1 comprising the additional step of also measuring pressure in said lung system by measuring pressure in said first gas line during expiration.

3. A ventilator system comprising:

an inspiratory line;

an expiratory line;

a connector device adapted for placement in the trachea of a patient, facing the carina, said connector device having a first gas line connected to said inspiratory line and a second gas line connected to said expiratory line;

means for permitting gas to flow in said inspiratory line and said first gas only in a direction toward said patient;

means for permitting gas to flow in said second gas line and in said expiratory gas line only in a direction away from said patient; and an expiratory pressure meter disposed in said expiratory line for measuring pressure in the lungs of said patient by measuring pressure in said expiration line during inspiration.

4. A ventilator system as claimed in claim 3 wherein said first gas line comprises a tracheotomy connector, and wherein said second gas line comprises a tracheal tube.

5. A ventilator system as claimed in claim 3 further comprising an inspiratory pressure meter disposed in said inspiratory line for measuring pressure in the lungs of the patient by measuring pressure in said inspiratory line during expiration.

6. A ventilator system as claimed in claim 5 wherein said first gas line has a smaller cross-section than said second gas line.

7. A ventilator system as claimed in claim 3 further comprising:

a valve system connected to said inspiratory line for supplying a predetermined flow of gas through said inspiratory line;

a first flow meter disposed for measuring a flow of said gas in said inspiratory line;

a second flow meter disposed in said expiratory line for measuring a flow of gas in said expiratory line; and said valve system comprising means for supplying said predetermined flow of gas during at least a latter portion of an expiratory phase and when said flow measured by said second flow meter falls below a threshold value.

8. A ventilator system as claimed in claim 7 wherein said second flow meter comprises means for measuring a peak value of said gas flow through said expiratory line during said expiratory phase and for setting said threshold value as a percentage of said peak value.

9. A ventilator system as claimed in claim 3 wherein said first gas line has a smaller cross-section than said second gas line.

10. A ventilator system as claimed in claim 3 wherein said connector device comprises a tracheal tube.

11. A ventilator system as claimed in claim 10 wherein said first gas line is disposed inside said second gas line.

12. A ventilator system as claimed in claim 10 wherein said first gas line is disposed along side and parallel to said second gas line.

* * * * *